United States Patent
Tomiyama et al.

(10) Patent No.: US 10,278,913 B2
(45) Date of Patent: May 7, 2019

(54) OIL-BASED EYELASH COSMETIC AND COSMETIC METHOD

(71) Applicant: JO Cosmetics Co., Ltd., Tokyo (JP)

(72) Inventors: Yumi Tomiyama, Tokyo (JP); Mizuyo Inoue, Tokyo (JP); Akihiro Nakano, Tokyo (JP); Hazuki Uchida, Tokyo (JP); Satoshi Haramizu, Tokyo (JP)

(73) Assignee: JO Cosmetics Co., Ltd., Tokyo (JP)

( * ) Notice: Subject to any disclaimer, the term of this patent is extended or adjusted under 35 U.S.C. 154(b) by 0 days.

(21) Appl. No.: 16/070,026

(22) PCT Filed: Jan. 13, 2017

(86) PCT No.: PCT/JP2017/000904
§ 371 (c)(1),
(2) Date: Jul. 13, 2018

(87) PCT Pub. No.: WO2017/122756
PCT Pub. Date: Jul. 20, 2017

(65) Prior Publication Data
US 2019/0054006 A1   Feb. 21, 2019

(30) Foreign Application Priority Data
Jan. 16, 2016 (JP) .................. 2016-006697

(51) Int. Cl.
| | |
|---|---|
| *A61K 8/92* | (2006.01) |
| *A61K 8/81* | (2006.01) |
| *A61K 8/73* | (2006.01) |
| *A61K 8/86* | (2006.01) |
| *A61K 8/88* | (2006.01) |
| *A61K 8/34* | (2006.01) |
| *A61K 8/31* | (2006.01) |
| *A61Q 1/10* | (2006.01) |
| *A61K 8/25* | (2006.01) |

(52) U.S. Cl.
CPC .................. *A61K 8/92* (2013.01); *A61K 8/25* (2013.01); *A61K 8/31* (2013.01); *A61K 8/34* (2013.01); *A61K 8/73* (2013.01); *A61K 8/8111* (2013.01); *A61K 8/86* (2013.01); *A61K 8/88* (2013.01); *A61K 8/927* (2013.01); *A61Q 1/10* (2013.01)

(58) Field of Classification Search
CPC .......... A61K 8/92; A61K 8/8111; A61K 8/73; A61K 8/76; A61K 8/88; A61K 8/34; A61K 8/927; A61K 8/31; A61K 8/25; A61Q 1/10
See application file for complete search history.

(56) References Cited

U.S. PATENT DOCUMENTS

2006/0130248 A1   6/2006   Pays et al.

FOREIGN PATENT DOCUMENTS

| JP | 2005-112770 A | 4/2005 |
|---|---|---|
| JP | 2006-176506 A | 7/2006 |
| JP | 2006-265216 A | 10/2006 |
| JP | 2006-306829 A | 11/2006 |
| JP | 2009-155224 A | 7/2009 |
| JP | 2012-140338 A | 7/2012 |

OTHER PUBLICATIONS

International Search Report of PCT/JP2017/000904 dated Feb. 14, 2017 [PCT/ISA/210], English Translation.

*Primary Examiner* — Trevor Love
(74) *Attorney, Agent, or Firm* — Sughrue Mion, PLLC

(57) ABSTRACT

An oil-based eyelash cosmetic including 22 to 50% by mass of a wax (A) containing a wax having a melting point of 50° C. to less than 70° C. (A-1) and a wax having a melting point of 70° C. to 110° C. (A-2), 0.1 to 10% by mass of a nonionic surfactant having an HLB value of 6 to 12 (B), 20 to 70% by mass of a volatile oil (C) and 0 to 5% by mass of water (E), and having the ratio by mass of the component (A-1) to the component (A-2) [(A-1)/(A-2)] of 1/0.2 to 1/5, is excellent in removability by warm water as well as volume effect, curling effect and long-lasting performance of cosmetic effect such as water resistance.

9 Claims, No Drawings

OIL-BASED EYELASH COSMETIC AND COSMETIC METHOD

CROSS REFERENCE TO RELATED APPLICATIONS

This application is a National Stage of International Application No. PCT/JP2017/000904, filed Jan. 13, 2017, claiming priority based on Japanese Patent Application No. 2016-006697, filed Jan. 16, 2016.

DETAILED DESCRIPTION OF THE INVENTION

Technological Field

The present invention relates to an oil-based eyelash cosmetic and a cosmetic method for making up eyelashes using the same, and more specifically, relates to an oil-based eyelash cosmetic excellent in removability by washing with warm water and a cosmetic method for making up with the same in which makeup can be easily removed by washing with warm water.

BACKGROUND TECHNOLOGY

An eyelash cosmetic, a representative of which is mascara, has a makeup effect to make eyes striking by curling eyelashes upwards or making the eyelashes thick and long. Conventionally, various types of eyelash cosmetics such as oil-based type, water-in-oil emulsion type, oil-in-water emulsion type and aqueous type have been known. In recent years, a mascara of the oil-in-water emulsion type that can be easily removed with warm water without using a special remover has become popular.

However, the mascara of the oil-in-water emulsion type has a problem that curling imparted to the eyelashes is hard to be maintained while the mascara is excellent in removability (cleansing property), that is, makeup using it can be readily removed. This is because the eyelashes which are physically curled by using a tool such as an eyelash curler lose the curling imparted due to contact with moisture.

On the other hand, the oil-based eyelash cosmetic has an excellent curl-retaining effect as compared with the eyelash cosmetic of the emulsion type such as the oil-in-water type or the water-in-oil type, and also is excellent in long-lasting performance of cosmetic effects such as water resistance (refer to Patent Document 1, paragraph 0009). However, the oil-based eyelash cosmetic has a disadvantage that a special remover is necessary for removing makeup. Hence, studies to improve the removability of the makeup have been intensively conducted. As a solution to the problem, there is proposed an oil-based eyelash cosmetic wherein a sufficient removability for removing makeup with warm water is imparted by blending an oil-soluble resin, a fatty acid soap, a nonionic surfactant having an HLB value of 12 or more and a volatile oil (refer to Patent Document 2). However, according to experiments by the inventors of the present invention, oil-based eyelash cosmetics prepared by using a surfactant such as a fatty acid soap or nonionic surfactant having a high HLB value did not yet exhibit a sufficient removability, and were insufficient in water resistance against sweat and tears.

Further, Patent Document 3 proposes an oil-based eyelash cosmetic containing a wax having a melting point of 55° C. to 70° C., a nonionic surfactant having an HLB value of 5 to 10, and a volatile hydrocarbon oil, and describes that the cosmetic is improved in volume effect, curl-retaining effect and long-lasting performance of cosmetic effects (refer to Patent Document 3). This patent document describes that, in addition to the wax having a melting point of 55° C. to 70° C., a wax having a melting point of more than 70° C. can be used together for adjusting viscosity of the cosmetic or strength of makeup film obtained after drying. However, the patent document also describes that the amount thereof is preferably less than 15% by mass with respect to the mass of the wax having a melting point of 55° C. to 70° C., and, in particular, it is preferred that the wax is substantially not incorporated (refer to paragraph 0017).

Also, Patent Document 4 discloses an oil-based mascara that contains 16.0% of beeswax (melting point 60° C. to 67° C.), 5.5% of high melting point microcrystalline wax (melting point 87° C. to 93° C.), 2.0% of rice bran (melting point 78° C. to 82° C.) and 1.0% of both end-modified organopolysiloxane (melting point 71° C. to 75° C.) as a wax component, and further contains a nonionic surfactant having an HLB value of 6, black iron oxide and the like (refer to Examples 1 to 3). This oil-based mascara contains 16% to 19% by mass of water.

PRIOR ART DOCUMENT

Patent Document

Patent Document 1: Japanese Unexamined Patent Publication No. 2006-306829
Patent Document 2: Japanese Unexamined Patent Publication No. 2006-265216
Patent Document 3: Japanese Unexamined Patent Publication No. 2012-140338
Patent Document 4: Japanese Unexamined Patent Publication No. 2009-155224

DISCLOSURE OF THE INVENTION

Problems to be Solved by the Invention

The present invention was completed under the aforementioned background, and it is therefore an object of the present invention to provide an oil-based eyelash cosmetic capable of imparting removability that is sufficient for removing makeup with only warm water without use of a special remover in the same manner as an eyelash cosmetic of the oil-in-water type while maintaining excellent curl effect and water resistance peculiar to conventional oil-based eyelash cosmetics.

Means Used to Solve the Problem

As a result of intensive studies to solve the above-mentioned problems, the present inventors have found that use of a combination of waxes having a different melting point from each other and use of a nonionic surfactant having a specific HLB value as a surfactant result in an oil-based eyelash cosmetic that is excellent in cosmetic effect (volume effect) to make the eyelashes thick and curling effect, and makeup using the oil-based eyelash cosmetic can be easily removed by cleansing with warm water despite exhibiting good water resistance. The present invention was completed based on the above knowledge.

Thus, the present invention provides an oil-based eyelash cosmetic comprising 22 to 50% by mass of a wax (A) containing a wax having a melting point of 50° C. to less than 70° C. (A-1) and a wax having a melting point of 70°

C. to 110° C. (A-2), 0.1 to 10% by mass of a nonionic surfactant having an HLB value of 6 to 12 (B), 20 to 70% by mass of a volatile oil (C) and 0 to 5% by mass of water (E), wherein the ratio by mass of the component (A-1) to the component (A-2), which is represented by (A-1)/(A-2), is 1/0.2 to 1/5. The present invention also provides a cosmetic method for making up eyelashes comprising a makeup for the eyelashes using the oil-based eyelash cosmetic, and removal of the makeup by washing with warm water without using a remover.

Effect of the Invention

The oil-based eyelash cosmetic of the present invention is excellent in removability by warm water in addition to excellent volume effect, curling effect and cosmetic retention (water resistance) peculiar to the conventional oil-based eyelash cosmetics. Further, according to the cosmetic method of the present invention, makeup can be easily removed by cleansing with warm water without using a special remover.

EMBODIMENTS FOR CARRYING OUT THE INVENTION

The oil-based eyelash cosmetic of the present invention contains a wax having a melting point of 50° C. or more and less than 70° C. (A-1), a wax having a melting point of 70° C. or more and 110° C. or less (A-2), a nonionic surfactant having an HLB value of 6 to 12 (B) and a volatile oil (C) as an essential component, and optionally contains water. As to the amount of water, an upper limit is defined.
(Wax)

In the present invention, the wax of component (A) is a combination of the wax having a melting point of 50° C. or more and less than 70° C. (A-1) and the wax having a melting point of 70° C. or more and 110° C. or less (A-2). As the wax, animal wax, vegetable wax, mineral wax, silicone wax, synthetic wax and the like can be used. The melting point of the wax is a value measured according to a second method of the melting point measurement method which is a general test method defined in quasi-drug raw material standards.

Examples of the component (A-1) include bees wax, paraffin wax, silicone wax and the like. Examples of commercially available waxes include bees wax such as SA Bees wax-PA (melting point 60° C. to 67° C.) available from Croda Japan K.K., Golden Brand (melting point 60° C. to 67° C.) and White Beeswax (melting point 60° C. to 63° C.) available from Miki Chemical Industry & Co., Ltd.; paraffin wax such as Paraffin Wax 135 (melting point 57° C. to 60° C.), Paraffin Wax 140 (melting point 60° C. to 63° C.), Paraffin Wax 150 (melting point 66° C. to 68° C.) and HNP-11 (melting point 66° C. to 70° C.) available from Nippon Seiro Co., Ltd.; and silicone wax such as SF 1642 (melting point 60° C. to 70° C.) available from Momentive Performance Materials Japan Ltd. These waxes can be used solely or in combination as appropriate.

On the other hand, examples of the component (A-2) include shellac wax, rice bran wax, carnauba wax, candelilla wax, japan wax, sunflower seed wax, orange wax, lemon wax, ceresin, paraffin wax other than the above, microcrystalline wax, polyethylene wax, Fischer-Tropsch wax, ethylene-propylene copolymer, silicone wax and synthetic beeswax. Examples of commercially available waxes include carnauba wax such as deodorized and purified carnauba wax No. 1 (melting point 80° C. to 86° C.) available from Cerarica Noda Co., Ltd.; micro crystalline wax such as HNP-9 (melting point 74° C. to 78° C.), Hi-Mic-1070 (melting point 77° C. to 82° C.), Hi-Mic-1080 (melting point 82° C. to 88° C.), Hi-Mic-2065 (melting point 72° C. to 78° C.), Hi-Mic-1090 (melting point 86° C. to 90° C.), HNP-0190 (melting point 87° C. to 93° C.) all of which are available from Nippon Seiro Co., Ltd. and Multiwax W-445 (melting point 77° C. to 82° C.) available from Sonneborn Co., Ltd.; polyethylene wax such as PERFORMALENE 400 (melting point 70° C. to 90° C.), 500 (melting point 83° C. to 92° C.), 655 (melting point 93 to 102° C.) all of which are available from NEW PHASE TECHNOLOGIES. These waxes can be used solely or in combination as appropriate.

The content of the wax of the component (A) is 22 to 50%, preferably 23 to 45%, more preferably 25 to 40%, by mass with respect to the whole cosmetic. When the content of the component (A) is excessively small, it becomes difficult to produce a cosmetic that exhibits sufficient properties in volume effect, curling effect and water resistance. When it is excessively large, removal of makeup by warm water and application of a cosmetic to the eyelashes become difficult.

The ratio of the component (A-1) having a melting point of 50° C. or more and less than 70° C.) and the component (A-2) having a melting point of 70° C. or more and 110° C. or less, which is represented by (A-1):(A-2), is 1:0.2 to 1:5, preferably 1:0.4 to 1:4, more preferably 1:0.6 to 1:3. When the ratio of (A-1) is excessively large, water resistance deteriorates, and when the ratio of (A-2) is excessively large, removability by warm water deteriorates.

The wax of the component (A-1) may be a single wax or an appropriate combination of a plurality of waxes. The whole wax constituting the component (A-1) has preferably an average melting point of 55° C. to 67° C., more preferably 57° C. to 65° C. When the average melting point is excessively low, it becomes difficult to produce a cosmetic having sufficient water resistance. When it is excessively high, application of a cosmetic to the eyelashes becomes difficult.

Like the component (A-1), the wax of the component (A-2) also may be a single wax or an appropriate combination of a plurality of waxes. The whole wax constituting the component (A-2) has preferably an average melting point of 75° C. to 95° C., more preferably 78° C. to 92° C. When the average melting point is excessively low, water resistance deteriorates, and when it is excessively high, removability by warm water deteriorates.

Here, the term "average melting point" relating to each of the component (A-1) and the component (A-2) means a melting point of a single wax when only one type of wax is used in each component, and means a weighted average value of melting points of a plurality of waxes used when two or more waxes are used in combination in each component. In the case of using a wax whose melting point is indicated with a range, the median value of the range is taken as a melting point of the wax.

The content of the component (A-1) is usually 5% to 30%, preferably 7% to 25%, more preferably 10% to 20%, by mass with respect to the whole cosmetic. When the content of component (A-1) is excessively small, the volume effect becomes poor, and removability by warm water tends to decrease due to increased proportion of the component (A-2). Conversely, when it is excessively large, water resistance tends to be insufficient and the curling effect also tends to be lowered.

The content of the component (A-2) is usually 3% to 30%, preferably 5% to 25%, more preferably 8% to 22%, by mass with respect to the whole cosmetic. When the content of component (A-2) is excessively small, water resistance and curling effect tend to be lowered. Conversely, when it is excessively large, removability by warm water tends to be lowered.

(Surfactant)

In the present invention, a nonionic surfactant is used as the component (B). The nonionic surfactant used has an HLB value in the range of 6 to 12, preferably 7 to 10. If the nonionic surfactant has an HLB that is out of this range, removability of makeup by warm water cannot be improved. Even if an anionic surfactant or a cationic surfactant is used in place of the nonionic surfactant, an eyelash cosmetic having excellent removability by warm water cannot be obtained.

Examples of the nonionic surfactant used as the component (B) include polyglycerol fatty acid esters such as polyglyceryl-4 stearate, polyglyceryl-10 distearate and polyglyceryl-2 oleate; polyoxyethylene hydrogenated castor oil such as PEG-10 hydrogenated castor oil and PEG-20 hydrogenated castor oil; polyoxyethylene fatty acid esters such as PEG-5 stearate and PEG-6 isostearate; polyoxyethylene alkyl ethers such as ceteth-2, oleth-2 and steareth-15; fatty acid polyoxyethylene alkyl ethers such as steareth-12 stearate and laureth-10 isostearate; polyoxyethylene fatty acid glyceryl such as PEG-6 glyceryl isostearate, PEG-20 glyceryl triisostearate and PEG-20 glyceryl tristearate; fatty acid polyoxyethylene hydrogenated castor oil such as PEG-20 hydrogenated castor oil isostearate, PEG-20 hydrogenated castor oil triisostearate; polyoxyethylene sorbitan fatty acid ester, polyoxyethylene polyoxypropylene copolymer, ether of polyoxyethylene polyoxypropylene copolymer and long-chain alcohol, ether of polybutylene glycol polyglycerin copolymer and long-chain alcohol, and the like. Of these, polyoxyethylene fatty acid ester, polyoxyethylene fatty acid glyceryl and fatty acid polyoxyethylene alkyl ether are preferably used.

When the nonionic surfactant contains a fatty acid residue in its molecule, it is preferably a residue of a higher fatty acid having 10 to 22 carbon atoms such as myristic acid, palmitic acid, stearic acid, isostearic acid and oleic acid. Examples of commercial products suitably used as the component (B) include Emalex GWS-320 (PEG-20 glyceryl tristearate; Nihon Emulsion Co., Ltd.; HLB 8), UNIOX GT-20IS (PEG-20 glyceryl isostearate; NOF Corporation; HLB 8), EMALEX PEIS-6EX (PEG-6 isostearate; Nihon Emulsion Co., Ltd.; HLB 9), and EMALEX SWS-12 (steareth-12 stearate; Nihon Emulsion Co., Ltd.; HLB 8).

The component (B) may be used alone or in combination of two or more. The content of the component (B) used is 0.1 to 10% by mass, preferably 0.5 to 8% by mass, and more preferably 1 to 6% by mass in the whole composition. When the content is excessively small, removability by warm water decreases, whereas when it is excessively large, water resistance decreases.

In the present invention, in addition to the component (B), a nonionic surfactant having an HLB value of more than 12, an anionic surfactant, a cationic surfactant or an amphoteric surfactant can be appropriately used in combination. Since these surfactants sometimes lower water resistance of the cosmetic, in the case of containing these surfactants, the content thereof is preferably limited to 2% or less, more preferably 0.5% or less, further more preferably 0.1% or less, by mass with respect to the whole composition. In particular, it is preferred to limit the content to 0.05% or less by mass. On the other hand, a nonionic surfactant having an HLB value of less than 6 may be contained as appropriate since it functions as an oil component. But, the content thereof is preferably 10% or less by mass with respect to the whole composition since curling effect decreases when it is excessively large.

(Volatile Oil)

The volatile oil used as the component (C) in the present invention is not limited as long as it is used in conventional cosmetics. The volatile oil usually has a boiling point at normal pressure of 60° C. to 260° C., preferably 100° C. to 220° C. Examples thereof include hydrocarbon oils such as isododecane, isohexadecane and saturated isoparaffin-type hydrocarbon oils containing a compound having 8 to 16 carbon atoms as a main component (e.g. hydrogenated polyisobutene); and volatile silicone oils. Examples of commercially available products include Marcasol R available from Maruzen Petrochemical Co., Ltd., IP Solvent 1620 and IP Solvent 2028, both of them are available from Idemitsu Kosan Co., Ltd., and the like. Of these, in view of storage stability and volatilization rate, isododecane and hydrogenated polyisobutene containing a compound having 8 to 16 carbon atoms as a main component are preferably used.

The content of the component (C) used is 20 to 70%, preferably 30 to 65%, more preferably 35 to 60%, by mass with respect to the whole composition. If the content is excessively small, an eyelash cosmetic having an appropriate viscosity cannot be obtained, and if a nonvolatile oil is added as a viscosity adjustor, curl effect and water resistance are lowered. Conversely, if the content is excessively large, an amount of residual components on the eyelashes is reduced, thereby volume effect and curl effect decrease.

In the present invention, in addition to the above components (A) to (C), an oil-soluble resin can be blended as the component (D). The oil-soluble resin is not particularly limited as long as it is soluble in oily components which form a continuous phase. For example, there can be mentioned silicone resin such as trimethylsiloxysilicate, partially crosslinked organopolysiloxane, trimethylsiloxysilylpropyl carbamic acid, fluorine modified silicone, acrylic modified silicone, silicone dendrimer modified resin compound; rosin acid resin such as pentaerythrityl rosinate; Candelilla resin; polyvinyl acetate type resin; polyvinyl isobutyl ether; polyisobutylene; and the like. Here, Candelilla resin means a resin component obtained by separating and extracting Candelilla wax with an organic solvent, and has a resin content of preferably 65% or more, more preferably 85% or more. Examples of commercially available Candelilla resin include Candelilla resin E-1 available from Japan Natural Products Inc.

The oil-soluble resins may be used alone or in combination of two or more, and the content thereof is preferably from 0.1 to 30% by mass, more preferably from 0.5 to 25% by mass, particularly preferably from 1 to 20% by mass with respect to the whole composition. By using the component (D) within this range, it is possible to further improve volume effect, curl-retaining effect and long-lasting performance of cosmetic effect.

The oil-based eyelash cosmetic composition of the present invention may contain a small amount of water as the component (E). The content of water is 5% or less, preferably 0.1 to 3%, by mass with respect to the whole cosmetic. When the content is within the range, the nonionic surfactant (B) and water form a solubilized state, that is, a state where oily components are present as a dispersion medium and the component (B) and water form reversed micelles. As a result, the nonionic surfactant of the component (B) is readily dissolved in the oil phase formed by the component (A) and the component (C), and thereby, separation and precipitation of the component (B) hardly occur even in storage for a long period of time, and storage stability is improved.

In the cosmetic of the present invention, a coloring material can be blended as the component (F). The coloring material is not particularly limited by its shape, particle diameter, and particle structure as long as it is commonly used in the field of cosmetics. Examples of the shape include a spherical shape, a plate shape, and a needle shape. Examples of the particle size include an aerosol, a fine particle and a pigment grade. The particle structure may be porous or nonporous.

Examples of the colorant (F) include inorganic powders, glittering powders, organic powders, pigment powders, metal powders, composite powders, and the like. More specifically, there can be mentioned inorganic pigments such as talc, mica, kaolin, calcium carbonate, silica, zinc oxide, titanium dioxide, red iron oxide, yellow iron oxide, black iron oxide, ultramarine blue, iron blue, carbon black, low order titanium oxide, cobalt violet, chromium oxide, chromium hydroxide, cobalt titanate, bismuth oxychloride and titanium-mica-based pearl pigment; resin powders of organic polymer such as polyamide resin, polyethylene resin, polyacryl resin, polyester resin, fluorine resin, cellulose resin, polystyrene resin, copolymer resin such as styrene-acryl copolymer resin, polypropylene resin, silicone resin, urethane resin; organic pigment such as Red No. 201, Red No. 202, Red No. 204, Red No. 205, Red No. 220, Red No. 226, Red No. 228, Red No. 405, Orange No. 203, Yellow No. 205, Yellow No. 4, Yellow No. 5, Blue No. 1, Blue No. 404, Green No. 3, zirconium lake thereof, barium lake thereof or aluminum lake thereof; natural coloring materials such as chlorophyll and β-carotene; dyes and the like. These coloring materials may be used alone or in combination of two or more. Of these, black coloring materials, particularly black iron oxide and carbon black are preferably used.

The content of the colorant (F) can be appropriately selected. It is preferably 0.1 to 20%, more preferably 0.5 to 15%, by mass with respect to the whole composition. When the content of the coloring material is excessively large, adhesion tends to be lowered. Conversely, when it is excessively small, coloring effect sometimes becomes insufficient.

In addition to the above components, the oil-based eyelash cosmetic of the present invention may contain components which are used in conventional cosmetics, for example, additives such as waxes other than the component (A), liquid oils other than the component (C), oily gelling agents, polyhydric alcohols, lower alcohols, ultraviolet absorbers, ultraviolet scattering agents, humectants, fragrances, antioxidants, preservatives, sequestering agents, defoaming agents, fibers, dyes, various extracts as long as they do not substantially impair the effect of the present invention.

Examples of the liquid oils other than the component (C) include oils, which are liquid at room temperature, such as a nonvolatile ester oil, a nonvolatile hydrocarbon oil, a nonvolatile silicone oil, a nonvolatile fluorine oil, an animal or vegetable oil. However, when these liquid oils are contained in a large amount, the water resistance and the curling effect tend to be lowered. Therefore, in the case of containing the liquid oils, the content thereof is preferably 5% or less, more preferably 2% or less, by mass with respect to the whole cosmetic. In particular, the cosmetic is preferred to be substantially free of the liquid oils. Examples of the oily gelling agent include dextrin fatty acid esters, sucrose fatty acid esters, starch fatty acid esters, aluminum stearate, organic modified clay minerals such as disteardimonium hectorite, and the like. The oily gelling agent can be appropriately used to improve stability and usability.

The oil-based eyelash cosmetic of the present invention can be prepared in accordance with conventional methods. For example, it can be prepared by combining all of the raw materials and heating the resultant mixture to a temperature higher than the melting point of the wax, and cooling the mixture with uniform stirring. Also the oil-based eyelash cosmetic can be prepared by preliminarily mixing the coloring materials with a part of the oil component and/or the surfactant component, subsequently combining the resultant mixture with the remaining components, and heating the mixture.

The oil-based eyelash cosmetic can be used as a mascara, a mascara makeup base, a mascara top coat, an eyelash essence and the like. The form of the cosmetic may be appropriately selected in accordance with its application. For example, the form can be creamy, liquid or the like. The oil-based eyelash cosmetic of the present invention can be applied to the eyelashes using appropriate tools such as brushes, resin molding applicators made of plastics, applicators made of metals and the like.

In the case of making up the eyelashes using the oil-based eyelash cosmetic of the present invention, makeup can be readily removed by using warm water of about 35° C. to 45° C. without using a remover which is usually used for removing a makeup of oil-based eyelash cosmetics.

EXAMPLES

Hereinafter, the present invention will be further described with reference to Examples and Comparative Examples, but the present invention is not limited by these Examples. The content of each ingredient in formulations in the following description is expressed in % by mass with respect to the whole composition unless otherwise specified.

The evaluation methods of the oil-based eyelash cosmetic in the following Examples and Comparative Examples are as follows.
(Evaluation Methods a to e)

As to the following evaluation items a to e, ten evaluators applied each sample to their own eyelashes, and scored at seven levels of from 0 to 6 based on the evaluation criteria shown in (1) below. Using the total score of 10 evaluators, properties as an oil-based eyelash cosmetic were evaluated according to the 4-step criterion shown in (2) below. The water resistance of the evaluation item c was evaluated based on the degree of bleeding of the cosmetic at 6 hours after application, and the curl-retaining effect of the evaluation item d was evaluated based on the curling state at 6 hours after application. Further, the removability I by warm water of 40° C. in the evaluation item e was evaluated by immersing a commercial cotton into warm water (tap water) of 40° C., sandwiching the eyelashes to which a sample was applied by the cotton for 30 seconds, wiping off the sample, and visually observing the residual amount of the sample on the eyelashes.
(Evaluation Item)
a. Volume effect
b. Curling effect
c. Water resistance (normal temperature) I
d. Curl-retaining effect
e. Removability by warm water of 40° C. I (1) Evaluation Criteria
(Rating): (Evaluation)
6: Very good
5: Good
4: Slightly good
3: Normal
2: Somewhat bad
1: Bad
0: Very bad
(2) Four-Grade Criteria
(Evaluation): (Total Score of Evaluation Score)
  ⊚: Total point is 46 to 60 points
  ○: Total points is 31 to 45 points
  Δ: Total points is 16 to 30
  x: Total points is 0 to 15
(Evaluation Methods f to g)

As to the removability and water resistance by warm water of 40° C., in addition to the evaluation of the evaluation items e or c, the evaluations shown in the following f or g were carried out, respectively.

Evaluation Method f: Water Resistance at Normal Temperature II

Using a commercial cotton immersed into tap water at 20° C., false eyelashes to which 0.005 g of each sample was applied were sandwiched by the cotton for 30 seconds. Then the false eyelashes were rubbed by the cotton 30 times from the base of the eyelash toward its tip end. The state of the sample transferred to the cotton was observed, and water resistance was evaluated according to the 4-step criterion shown in (3) below. The transfer amount of the sample to the cotton was estimated by visual observation in terms that a transfer amount obtained when the same test was performed using the cotton containing a sufficient amount of cleansing lotion (product name: Uruochimizu cleansing lotion, Mandom corporation) is 100%, and no transfer amount is 0%.

Evaluation Method g: Removability by Warm Water of 40° C. II

Using a commercial cotton immersed into tap water at 40° C., false eyelashes to which 0.005 g of each sample was applied were sandwiched by the cotton for 30 seconds. Then the false eyelashes were rubbed 30 times by the cotton from the base of the eyelash toward its tip end. The transfer amount of the sample to the cotton was estimated in the same manner as described above, and removability was evaluated according to the 4-grade criterion shown in (4) below.

(3) Four-Grade Criterion (Water Resistance Test)
(Evaluation): (Evaluation Criteria)
  ⊚: 10% or less
  ○: more than 10% to 50% or less
  Δ: more than 50% to 90% or less
  x: more than 90%

(4) Four-Grade Criteria (Removability Test by Warm Water)
(Evaluation): (Evaluation Criteria)
  ⊚: more than 90%
  ○: more than 50% to 90% or less
  Δ: more than 10% to 50%
  x: 10% or less Examples 1 to 5 and Comparative Examples 1 to 2

<Oil-Based Mascara>

Mascara of the formulation shown in Table 1 was prepared according to the following production procedure, and as to the cosmetic effect to make the eyelashes thick (volume effect and curl effect), its retention (water resistance and curling effect), the easiness on removal by warm water, sensory evaluation were carried out according to the foregoing method. The results are also shown in Table 1.

(Production Procedure)

(1) Ingredients contained in phases (A) to (D) shown in Table 1 were heated to about 110° C. and homogeneously mixed.

(2) Ingredients contained in phases (E) to (H) shown in Table 1 were added to the mixed solution obtained in the above (1) and homogeneously mixed.

(3) The mixture prepared in (2) above was filled into a container to form an oil-based mascara.

TABLE 1

| Phase | Component | | Example 1 | Example 2 | Example 3 | Example 4 | Example 5 | Comparative Example 1 | Comparative Example 2 |
|---|---|---|---|---|---|---|---|---|---|
| A | C | Hydrogenated polyisobutene (* 1) | Balance | Balance | Balance | Balance | Balance | Balance | Balance |
| | | Sucrose acetate stearate (* 10) | 1.5 | 1.5 | 1.5 | 1.5 | 1.5 | 1.5 | 1.5 |
| | A-1 | Paraffin (b.p. 57-60° C.) (* 2) | 15.0 | 23.0 | 20.0 | 8.0 | 5.7 | 29.0 | 27.0 |
| | A-1 | Bees wax (b.p. 60-67° C.) (* 3) | 0.9 | 0.9 | 0.9 | 0.9 | 0.9 | 0.9 | 0.9 |
| | | Total of (A-1) | (15.9) | (28.9) | (20.9) | (8.9) | (6.6) | (29.9) | (27.9) |
| | | Average melting point of (A-1) (° C.) | 58.8 | 58.7 | 58.7 | 59.0 | 59.2 | 58.7 | 58.7 |
| | A-2 | Microcrystalline wax | 2.0 | 0.9 | 1.3 | 3.0 | 3.3 | — | 0.3 |
| | A-2 | Microcrystalline wax ( b.p. : 86-90° C.) (* 5) | 9.0 | 3.9 | 5.8 | 13.5 | 15.0 | — | 1.3 |
| | A-2 | Polyethylene (m.p.:75-90° C.) (* 6) | 3.0 | 1.3 | 1.9 | 4.5 | 5.0 | — | 0.4 |
| | | Total of (A-2) | (14.0) | (6.0) | (9.0) | (21.0) | (23.3) | 0.0 | (2.0) |
| | | Average melting point of (A-2) (° C.) | 85.6 | 85.6 | 85.6 | 85.6 | 85.6 | — | 85.6 |
| | | (A-1) : (A-2) | 1: 0.88 | 1: 0.25 | 1: 0.43 | 1: 2.35 | 1: 3.53 | 1: 0 | 1: 0.07 |
| | | Tocopherol | 0.10 | 0.10 | 0.10 | 0.10 | 0.10 | 0.10 | 0.10 |

TABLE 1-continued

| | | | Example | | | | | Comparative Example | |
|---|---|---|---|---|---|---|---|---|---|
| Phase | | Component | 1 | 2 | 3 | 4 | 5 | 1 | 2 |
| B | | Dextrin myristate | 1.0 | 1.0 | 1.0 | 1.0 | 1.0 | 1.0 | 1.0 |
| C | C | Hydrogenated polyisobutene (* 1) | 12.0 | 12.0 | 12.0 | 12.0 | 12.0 | 12.0 | 12.0 |
| | | Ddisteardimonium hectorite | 2.0 | 2.0 | 2.0 | 2.0 | 2.0 | 2.0 | 2.0 |
| | | Ethanol | 1.0 | 1.0 | 1.0 | 1.0 | 1.0 | 1.0 | 1.0 |
| D | F | Dimethicone-coated black iron oxide | 5.0 | 5.0 | 5.0 | 5.0 | 5.0 | 5.0 | 5.0 |
| E | | Nylon fiber (* 7) | 0.3 | 0.3 | 0.3 | 0.3 | 0.3 | 0.3 | 0.3 |
| F | | Phenoxyethanol | 0.5 | 0.5 | 0.5 | 0.5 | 0.5 | 0.5 | 0.5 |
| G | E | Water | 2.0 | 2.0 | 2.0 | 2.0 | 2.0 | 2.0 | 2.0 |
| | | Pentylene glycol | 1.0 | 1.0 | 1.0 | 1.0 | 1.0 | 1.0 | 1.0 |
| | B | PEG-20 glyceryl tristearate (HLB: 8) (* 8) | 2.5 | 2.5 | 2.5 | 2.5 | 2.5 | 2.5 | 2.5 |
| H | D | Trimethylsiloxysilicate/ isododecane = 60/40 (* 9) | 1.0 | 1.0 | 1.0 | 1.0 | 1.0 | 1.0 | 1.0 |
| Evaluation | | Volume effect | ○ | Δ | ⊚ | ○ | ○ | x | x |
| | | Curling effect | ○ | ○ | ○ | ○ | ⊚ | x | Δ |
| | | Water resistance (Normal tempreture) I | ⊚ | ○ | ○ | ⊚ | ⊚ | x | Δ |
| | | Curl retention effect | ○ | ○ | ○ | ○ | ○ | Δ | Δ |
| | | Removability by warm water of 40° C. I | ○ | ○ | ○ | ○ | Δ | ⊚ | ○ |
| | | Water resistance (Normal tempreture) II | ⊚ | ○ | ⊚ | ⊚ | ⊚ | x | Δ |
| | | Removability by warm water (40° C.) II | ○ | ⊚ | ○ | Δ | Δ | ⊚ | ⊚ |

* 1: Product name IP Solvent 1620 (Idemitsu Kosan Co., Ltd.) (boiling point [distillation range]: 166 to 202° C.)
* 2: Product name Paraffin wax 135 (Nippon Seiro Co., Ltd.)
* 3: Product name WHITE BEES WAX (Miki Chemical Industry Co., Ltd.)
* 4: Product name Multiwax W-445 (Sonneborn)
* 5: Product name HI-MIC-1090 (Nippon Seiro Co., Ltd.)
* 6: Product name PERFORMALENE 400 POLTETHYLENE (NEW PHASE TECHNOLOGIES)
* 7: Product name Nylon Fiber 6D-2 MM (Cosmeterials Corporation)
* 8: Product name EMALEX GWS-320 (Nihon Emulsion Co., Ltd.)
* 9: Product name X-21-5595 (Shin-Etsu Chemical Co., Ltd.)
* 10: Product name Sugar Wax A-10E (Daiichi Kogyo Seiyaku Co., Ltd.)

As is apparent from the results shown in Table 1, the mascaras of Examples 1 to 5 are superior in volume effect, water resistance and curl retention effect as compared with the mascaras of Comparative Examples 1 and 2, and the mascaras of Examples 1 to 5 can be removed with warm water without using a special remover for a mascara. On the other hand, the mascaras of Comparative Example 1 in which the wax of the component (A) is not blended, and of Comparative Example 2 in which only 2% of the wax with a high melting point defined as the component (A-2) is blended, had unsatisfactory properties as to the water resistance, the curling effect, the volume effect and the retention of the cosmetic effect.

Examples 6 to 12 and Comparative Examples 3 to 8

<Oil-Based Mascara>

Mascaras of the formulation shown in Table 2 were prepared by the same production procedure as described above, and water resistance and removability by warm water were evaluated in accordance with the above evaluation methods f to g. The results are shown in Table 2 together with the formulation.

TABLE 2

| | | | Example | | | | | | | Comparative Example | | | |
|---|---|---|---|---|---|---|---|---|---|---|---|---|---|
| Phase | | Component | 6 | 7 | 8 | 9 | 10 | 11 | 12 | 3 | 4 | 5 | 6 |
| A | C | Hydrogenated polyisobutene (* 1) | Balance | Balance | Balance | Balance | Balance | Balance | Balance | Balance | Balance | Balance | Balance |
| | | Sucrose acetate stearate (* 10) | 1.5 | 1.5 | 1.5 | 1.5 | 1.5 | 1.5 | 1.5 | 1.5 | 1.5 | 1.5 | 1.5 |
| | A-1 | Paraffin (b.p. 57-60° C.) (* 2) | 15.0 | 15.0 | 15.0 | 15.0 | 15.0 | 15.0 | 15.0 | 15.0 | 15.0 | 15.0 | 15.0 |
| | A-1 | Bees wax (b.p. 60-67° C.) (* 3) | 0.9 | 0.9 | 0.9 | 0.9 | 0.9 | 0.9 | 0.9 | 0.9 | 0.9 | 0.9 | 0.9 |
| | | Total of (A-1) | (15.9) | (15.9) | (15.9) | (15.9) | (15.9) | (15.9) | (15.9) | (15.9) | (15.9) | (15.9) | (15.9) |

TABLE 2-continued

|  |  |  | Example | | | | | | | Comparative Example | | | |
|---|---|---|---|---|---|---|---|---|---|---|---|---|---|
| Phase | | Component | 6 | 7 | 8 | 9 | 10 | 11 | 12 | 3 | 4 | 5 | 6 |
|  | A-2 | Microcrystalline wax (b.p.: 77-82° C. (* 4) | 2.0 | 2.0 | 2.0 | 2.0 | 2.0 | 2.0 | 2.0 | 2.0 | 2.0 | 2.0 | 2.0 |
|  | A-2 | Microcrystalline wax (b.p.: 86-90° C.) (* 5) | 9.0 | 9.0 | 9.0 | 9.0 | 9.0 | 9.0 | 9.0 | 9.0 | 9.0 | 9.0 | 9.0 |
|  | A-2 | Polyethylene (m.p.:75-90° C.) (* 6) | 3.0 | 3.0 | 3.0 | 3.0 | 3.0 | 3.0 | 3.0 | 3.0 | 3.0 | 3.0 | 3.0 |
|  |  | Total of (A-2) | (14.0) | (14.0) | (14.0) | (14.0) | (14.0) | (14.0) | (14.0) | (14.0) | (14.0) | (14.0) | (14.0) |
|  |  | (A-1) : (A-2) | 1: 0.88 | 1: 0.88 | 1: 0.88 | 1: 0.88 | 1: 0.88 | 1: 0.88 | 1: 0.88 | 1: 0.88 | 1: 0.88 | 1: 0.88 | 1: 0.88 |
|  |  | Tocopherol | 0.1 | 0.1 | 0.1 | 0.1 | 0.1 | 0.1 | 0.1 | 0.1 | 0.1 | 0.1 | 0.1 |
| B |  | Dextrin myristate | 1.0 | 1.0 | 1.0 | 1.0 | 1.0 | 1.0 | 1.0 | 1.0 | 1.0 | 1.0 | 1.0 |
|  |  | Canderilla resin (* 19) | 2.0 | 2.0 | 2.0 | 2.0 | 2.0 | 2.0 | 2.0 | 2.0 | 2.0 | 2.0 | 2.0 |
| C | C | Hydrogenated polyisobutene (* 1) | 12.0 | 12.0 | 12.0 | 12.0 | 12.0 | 12.0 | 12.0 | 12.0 | 12.0 | 12.0 | 12.0 |
|  |  | Disteardimonium hectorite | 2.0 | 2.0 | 2.0 | 2.0 | 2.0 | 2.0 | 2.0 | 2.0 | 2.0 | 2.0 | 2.0 |
|  |  | Ethanol | 1.0 | 1.0 | 1.0 | 1.0 | 1.0 | 1.0 | 1.0 | 1.0 | 1.0 | 1.0 | 1.0 |
| D | F | Iron oxide/dimethicone = 98/2 | 5.0 | 5.0 | 5.0 | 5.0 | 5.0 | 5.0 | 5.0 | 5.0 | 5.0 | 5.0 | 5.0 |
| E |  | Nylon fiber (* 7) | 0.3 | 0.3 | 0.3 | 0.3 | 0.3 | 0.3 | 0.3 | 0.3 | 0.3 | 0.3 | 0.3 |
| F |  | Phenoxyethanol | 0.5 | 0.5 | 0.5 | 0.5 | 0.5 | 0.5 | 0.5 | 0.5 | 0.5 | 0.5 | 0.5 |
|  |  | Phenoxyethanol | 1.0 | 1.0 | 1.0 | 1.0 | 1.0 | 1.0 | 1.0 | 1.0 | 1.0 | 1.0 | 1.0 |
| G | E | Water | 2.0 | 2.0 | 2.0 | 2.0 | 2.0 | 2.0 | — | 2.0 | 2.0 | 2.0 | — |
|  | B | PEG-20 glyceryl tristearate (HLB: 8) (* 8) | 2.5 | — | — | — | — | — | 2.5 | — | — | — | — |
|  | B | PEG-20 glyceryl triisostearate (HLB: 8) (* 11) | — | 2.5 | — | — | — | — | — | — | — | — | — |
|  | B | Steareth-12 stearate (HLB: 8) (* 12) | — | — | 2.5 | — | — | — | — | — | — | — | — |
|  | B | PEG-6 glyceryl isostearate (HLB: 9) (* 13) | — | — | — | 2.5 | — | — | — | — | — | — | — |
|  | B | PEG-4 glyceryl tristearete (HLB: 2) (* 14) | — | — | — | — | — | — | — | 2.5 | — | — | — |
|  | B | PEG-20 triisostearate hydrogenated castor oil (HLB: 6) (* 15) | — | — | — | — | 2.5 | — | — | — | — | — | — |
|  | B | Steareth-15 (HLB: 12)(* 16) | — | — | — | — | — | 2.5 | — | — | — | — | — |
|  | B | Polysorbate 80 (HLB: 15) (* 17) | — | — | — | — | — | — | — | — | 2.5 | — | — |
|  | B | PEG-40 stearate (HLB: 17.5) (* 18) | — | — | — | — | — | — | — | — | — | 2.5 | — |
| H | D | Trimethylsiloxysilicate/isododecane = 60/40 (* 9) | 5.0 | 5.0 | 5.0 | 5.0 | 5.0 | 5.0 | 5.0 | 5.0 | 5.0 | 5.0 | 5.0 |
| Evaluation | | Water resistance (Normal tempreture) II | ◎ | ◎ | ◎ | ◎ | ◎ | Δ | ◎ | ◎ | Δ | x | ◎ |
|  | | Removability by warm water of 40° C. I | ◎ | ◎ | ◎ | ○ | Δ | Δ | ◎ | x | x | Δ | x |

* 11: Product name Uniox GT-20IS (NOF Corporation)
* 12: Product name EMALEX-SWS-12 (Nihon Emulsion? Co., Ltd.)
* 13: Product name EMALEX PEIS-6 EX (Nihon Emulsion Co., Ltd.)
* 14: Product name EMALEX-GWS-304 (Nihon? Emulsion Co., Ltd.)
* 15: Product name EMALEX RWIS-320 (Nihon Emulsion Co., Ltd.)
* 16: Product name EMALEX 615 (Nihon Emulsion Co., Ltd.)
* 17: Product name Rheodol TW-0 120V (Kao Corporation)
* 18: Product name NIKKOL MYS-40V (Nikko Chemicals Co., Ltd.)
* 19: Product name Candelilla resin E-1 (Japan Natural Products Co., Ltd.)

As is apparent from the results shown in Table 2, the mascaras of Examples 6 to 12 were excellent in water resistance and removability by warm water.

On the other hand, the mascaras of Comparative Example 3 in which a nonionic surfactant having an HLB value of 2 was blended, of Comparative Example 4 in which a nonionic surfactant having an HLB value of 15 was blended, and of Comparative Example 6 in which no nonionic surfactant was blended, had insufficient removability by warm water. Further, the mascara containing a nonionic surfactant having an HLB value of 17.5 of Comparative Example 5 was inferior in water resistance.

Example 11

<Mascara Makeup Base>

Using the ingredients shown below, a mascara makeup base was prepared according to the following production procedure.

| (Component) | (%) |
|---|---|
| (1) Isododecane (*20) | Balance |
| (2) Paraffin (melting point: 57 to 60° C.) (*2) | 7 |
| (3) Beeswax (melting point: 60 to 67° C.) (*3) | 10 |
| (4) Carnauba wax (melting point: 80 to 86° C.) (*21) | 7 |
| (5) Microcrystalline wax (melting point: 77 to 82° C.) | 3 |
| (6) Polyethylene (melting point: 75 to 90° C.) (*6) | 5 |
| (7) Tocopherol | 0.1 |
| (8) Talc | 5 |
| (9) Nylon fiber (*7) | 0.5 |
| (10) PEG-20 tristearate glyceryl (*8) | 2.5 |
| (11) Candelilla resin (*19) | 2 |
| (12) Trimethylsiloxysilicate/isododecane = 60/40 (*9) | 3 |
| (13) Dextrin palmitate | 1 |
| (14) Phenoxyethanol | 0.5 |

(*20): Product name CREASIL ID CG (CIT Sarl)
(*21): Product name Deodorized purified carnauba wax No. 1 (Cerarica Noda Co., Ltd.)
(Production procedure)
A. Components (1) to (14) were heated and homogeneously mixed at about 110° C.
B. The mixed solution obtained in the above A was filled into a container to form a mascara makeup base.

After applying the mascara makeup base obtained as described above to the eyelashes, a commercial mascara (Dejavu Fiber Wig Ultra Long a) was applied thereon. In this case, the mascara exhibited better curling effect and water resistance as compared with the case when no mascara makeup base was used. Further, when trying to remove the makeup only with warm water of about 40° C., the mascara makeup base was easily removed together with the mascara.

INDUSTRIAL APPLICABILITY

According to the present invention, there is provided an oil-based eyelash cosmetic having excellent removability by warm water in addition to excellent volume effect, curling effect and long-lasting performance of cosmetic effect such as water resistance peculiar to the conventional oil-based eyelash cosmetics. Further, when using this oil-based eyelash cosmetic, makeup can be easily removed by warm water without using a special remover, so makeup removal is efficient.

The invention claimed is:

1. An oil-based eyelash cosmetic comprising,
   22 to 50% by mass of (A) a wax which is a combination of (A-1) a wax having a melting point of 50° C. or higher and lower than 70° C. and (A-2) a wax having a melting point of 70° C. or higher and 110° C. or lower,
   0.1 to 10% by mass of (B) a nonionic surfactant having an HLB value of 7 to 10,
   20 to 70% by mass of (C) a volatile oil and
   0 to 5% by mass of (E) water,
   wherein a ratio by mass of the component (A-1) to the component (A-2), which is represented by (A-1)/(A-2), is 1/0.2 to 1/5.

2. The oil-based eyelash cosmetic according to claim 1, further comprising 0.1 to 30% by mass of (D) an oil-soluble resin.

3. The oil-based eyelash cosmetic according to claim 1, further comprising 0.1 to 20% by mass of (E) a coloring material.

4. The oil-based eyelash cosmetic according to claim 1, wherein the (A-1) component has an average melting point of 55° C. to 67° C. and the (A-2) component has an average melting point of 75° C. to 95° C.

5. The oil-based eyelash cosmetic according to claim 1, wherein the content of the (A-1) component is 5 to 30% by mass and the content of the (A-2) component is 3 to 30% by mass.

6. The oil-based eyelash cosmetic according to claim 1, wherein the content of the (E) component is 0.1 to 3% by mass.

7. The oil-based eyelash cosmetic according to claim 1, wherein the content of liquid oil other than the (C) component, which may be optionally contained, is 5% by mass or less.

8. The oil-based eyelash cosmetic according to claim 1, wherein it is a mascara or a makeup base therefor.

9. A process for making up eyelashes comprising makeup of eyelashes using the oil-based eyelash cosmetic according to claim 1, and removal of the makeup by washing with warm water without using a remover.

* * * * *